United States Patent
Liu et al.

(10) Patent No.: US 10,561,803 B2
(45) Date of Patent: Feb. 18, 2020

(54) ULTRASONIC ATOMIZER AND ELECTRONIC CIGARETTE

(71) Applicant: CHINA TOBACCO HUNAN INDUSTRIAL CO., LTD., Changsha, Hunan (CN)

(72) Inventors: Jianfu Liu, Hunan (CN); Kejun Zhong, Hunan (CN); Xiaoyi Guo, Hunan (CN); Wei Huang, Hunan (CN); Yuangang Dai, Hunan (CN); Xinqiang Yin, Hunan (CN); Hong Yu, Hunan (CN); Lizhou Shen, Hunan (CN); Yang Wang, Hunan (CN)

(73) Assignee: CHINA TOBACCO HUNAN INDUSTRIAL CO., LTD., Changsha, Hunan (CN)

( * ) Notice: Subject to any disclaimer, the term of this patent is extended or adjusted under 35 U.S.C. 154(b) by 118 days.

(21) Appl. No.: 15/577,650

(22) PCT Filed: Jun. 22, 2016

(86) PCT No.: PCT/CN2016/086687
§ 371 (c)(1),
(2) Date: Nov. 28, 2017

(87) PCT Pub. No.: WO2017/161715
PCT Pub. Date: Sep. 28, 2017

(65) Prior Publication Data
US 2018/0161525 A1   Jun. 14, 2018

(30) Foreign Application Priority Data

Mar. 21, 2016   (CN) .......................... 2016 1 0160216

(51) Int. Cl.
*A24F 13/00*     (2006.01)
*A61M 11/00*     (2006.01)
(Continued)

(52) U.S. Cl.
CPC ......... *A61M 11/005* (2013.01); *A24F 47/002* (2013.01); *A61M 15/001* (2014.02);
(Continued)

(58) Field of Classification Search
CPC ...................................................... A24F 47/00
(Continued)

(56) References Cited

U.S. PATENT DOCUMENTS

| 2012/0118301 A1 | 5/2012 | Montaser |
| 2018/0242644 A1* | 8/2018 | Bessant ............... H05B 1/0227 |
| 2019/0142063 A1* | 5/2019 | Liu ......................... A24F 47/00 |

FOREIGN PATENT DOCUMENTS

| CN | 2889333 Y | 4/2007 |
| CN | 203492790 U | 3/2014 |

(Continued)

OTHER PUBLICATIONS

International Search Report issued in International Application No. PCT/CN2016/086687 dated Dec. 22, 2016, 7 pages.

*Primary Examiner* — Phuong K Dinh
(74) *Attorney, Agent, or Firm* — Mauriel Kapouytian Woods LLP; James Woods (57) ABSTRACT

The present invention discloses an ultrasonic atomizer and electronic cigarette. The ultrasonic atomizer includes an atomization piece and a liquid guide structure, which guides liquid onto an upper surface of the atomization piece; the liquid guide structure communicates with a liquid storage cavity; the upper surface of the atomization piece communicates with an airflow passage; and the atomization piece comprises a piezoelectric ceramic layer and an electric conductor, which drives vibration of the piezoelectric ceramic layer. No micropore needs to be provided in the atomization piece of the present invention to eject the atomized gas, thereby being free of the situation that the (Continued)

micropore is blocked by larger atomized gas particles, resulting in that the atomized gas cannot be ejected, and meanwhile the situation of liquid leakage of the atomizer can be better prevented.

17 Claims, 6 Drawing Sheets

(51) Int. Cl.
*A61M 15/00* (2006.01)
*A24F 47/00* (2020.01)
*B05B 17/06* (2006.01)

(52) U.S. Cl.
CPC ..... *A61M 15/0085* (2013.01); *B05B 17/0661* (2013.01); *B05B 17/0684* (2013.01)

(58) Field of Classification Search
USPC .................................................. 131/328–329
See application file for complete search history.

(56) References Cited

FOREIGN PATENT DOCUMENTS

| | | | |
|---|---|---|---|
| CN | 203662023 | U | 6/2014 |
| CN | 204742639 | U | 11/2015 |
| CN | 105286090 | A | 2/2016 |
| CN | 105559151 | A | 5/2016 |
| CN | 205432145 | U | 8/2016 |
| CN | 107105784 | A | 8/2017 |
| JP | 2001069963 | A | 3/2001 |

* cited by examiner

ULTRASONIC ATOMIZER AND ELECTRONIC CIGARETTE

CROSS REFERENCE TO RELATED APPLICATIONS

This application is a national phase application of international application number PCT/CN2016/086687 filed on Jun. 22, 2016, which claims priority to Chinese application number 2016101602163 filed on Mar. 21, 2016. The entire contents of these applications are hereby incorporated herein by reference.

FIELD OF THE INVENTION

The present invention relates to an ultrasonic atomizer and electronic cigarette.

BACKGROUND OF THE INVENTION

The existing atomizers use heating wires to heat tobacco tar, the tobacco tar or liquid is guided onto the heating wires by tobacco tar guide cotton or fibers. When the temperatures of the heating wires are too high, the tobacco tar guide cotton or fibers and other tobacco tar guide materials are burnt easily to produce harmful substances, which damage the health of smokers, and burnt flavor is produced easily to affect the smoke taste; moreover, part of the heat of the heating wires will be absorbed by the tobacco tar guide materials, thereby resulting in the disadvantages of heat conduction loss, high power consumption and low efficiency, and the atomizers easily become hot.

BRIEF SUMMARY OF THE INVENTION

The technical problem to be solved in the present invention is to provide an ultrasonic atomizer and an electronic cigarette in view of the shortcomings of the prior art.

To solve the above-mentioned technical problem, the present invention adopts the technical solutions as follows: an ultrasonic atomizer, comprising an atomization piece and a liquid guide structure, which guides liquid onto the upper surface of the atomization piece; the liquid guide structure communicates with a liquid storage cavity; the upper surface of the atomization piece communicates with an airflow passage; and the atomization piece comprises a piezoelectric ceramic layer and an electric conductor, which drives vibration of the piezoelectric ceramic layer.

The atomization piece and the liquid storage cavity are sequentially arranged along an outflow direction of an atomized gas, and the liquid storage cavity is provided on the atomization piece, so that the liquid in the liquid storage cavity can flow onto the liquid guide structure more conveniently.

The airflow passage comprises an air inlet pipe and an air outlet pipe provided in the air inlet pipe, and an air inlet passage is provided between the inner wall of the air inlet pipe and the outer wall of the air outlet pipe; the bottom end of the air outlet pipe communicates with the atomization piece; top ends of the air inlet pipe and the air outlet pipe are in fixed connection with a suction nozzle base, and the air outlet pipe communicates with a suction nozzle on the suction nozzle base; an air inlet is provided in the suction nozzle base; and the air inlet passage communicates with the air inlet. The airflow passage can guarantee the external air to enter the air inlet passage from the air inlet, and then the external air is mixed with the smoke produced by atomization of the atomization piece at the bottom end of the air inlet passage and is transferred to the oral cavity of a user by the air outlet pipe and the suction nozzle, accordingly the structure is simple and the fabrication is convenient.

The liquid guide structure is in contact with the upper surface of the atomization piece, the bottom end of the air inlet pipe props against the upper surface of the liquid guide structure (i.e., the contact between the bottom end of the air inlet pipe and the liquid guide structure is contact in a pressure state), and an air inlet notch is provided in the bottom end of the air outlet pipe. An air outlet passage is provided in the air outlet pipe; and the air inlet passage communicates with the air outlet passage through the air inlet notch. The external air is guaranteed to enter the air outlet pipe in time to take away the smoke, so as to prevent the smoke from entering the air inlet passage to affect the taste of the smoke or generate a condensed tobacco tar accumulation.

The liquid guide structure comprises a porous material; the upper surface of the porous material covers or fills a liquid outlet in the bottom end of the liquid storage cavity; the porous material and/or the atomization piece is provided in an elastic sealing sleeve, and the outer wall of the upper part of the elastic sealing sleeve is in hermetical connection with the inner wall of the bottom end of the liquid storage cavity; and both of the liquid storage cavity and the elastic sealing sleeve are provided in a housing. The elastic sealing sleeve can seal and fix the atomization piece so as to prevent leakage of the liquid, and meanwhile the phenomenon can be avoided that the atomization piece cannot vibrate because it is clamped.

A hole is provided in the middle of the porous material, and the hole is provided below the air outlet pipe; and the lower surface of the porous material is in contact with the atomization piece through a liquid guide layer. The liquid guide layer can guarantee that the liquid can be guided to the middle of the atomization piece more uniformly.

There is a recessed region in the middle of the upper surface of the porous material, and the recessed region is located below the air outlet pipe. The contact between the liquid and the atomization piece is more sufficient, the liquid guide is more liable, and dry burning of the atomization piece can be well prevented.

The liquid guide structure comprises the porous material; the upper surface of the porous material is in contact with the lower surface of the atomization piece; and a plurality of liquid guide holes are provided in the atomization piece. The liquid permeates to the upper surface of the atomization piece through the liquid guide holes, the atomization piece can extrude the porous material while vibrating, so that the liquid can be supplemented to the upper surface of the atomization piece through the liquid guide holes quickly, so as to prevent a small smoke yield or a damage to the atomization piece resulting from insufficient liquid on the surface of the atomization piece.

The atomization piece and/or the porous material is provided in a mounting base; the top end of the mounting base is in fixed connection with the bottom end of the air inlet pipe; the bottom end of the mounting base is in fixed connection with the middle of a base; the lower surface of the porous material is in contact with the upper surface of the middle of the base; the outer wall of the base is in fixed connection with the inner wall of the bottom end of the liquid storage cavity; passages are provided among the mounting base, the inner wall of the liquid storage cavity and the inner wall of the base; a liquid inlet is provided in the bottom of the mounting base; and the liquid inlet communicates with the liquid storage cavity through the passages. The atomization piece mounting structure and the airflow passage are of an integrated structure, thereby being convenient to fabricate.

A regulating device, which regulates the amount of the air inflow of the air inlet is provided on the suction nozzle base, and the amount of the airflow of the air inlet can be regulated by the regulating device, therefore the taste of the atomized gas can be improved.

A tobacco tar injection hole is provided in the liquid storage cavity to facilitate supplement of the liquid when there is no liquid in the liquid storage cavity.

The electric conductor is in elastic connection with a positive electrode and a negative electrode fixed in the base. The elastic connection can well prevent an open circuit resulting from melt of a bonding pad because of high temperature or vibration generated in a working process of the atomization piece to produce.

The atomization piece is in contact with a temperature sensor, the temperature sensor can sense the temperature of the atomization piece, and thus the start and stop of the atomization piece can be controlled conveniently to prevent the atomization piece from being damaged.

Correspondingly, the present invention further provides an electronic cigarette, comprising a power supply component and the above-mentioned ultrasonic atomizer, the power supply component provides working power supply for the atomization piece and the temperature sensor.

The power supply component and the ultrasonic atomizer can be vertically provided, and can also be provided side by side in a shell, and the volume is smaller and the space utilization rate is higher if the power supply component and the ultrasonic atomizer are provided side by side.

A liquid storage cavity observation window is provided in the shell to facilitate observation of the conditions in the liquid storage cavity.

Compared with the prior art, the present invention has the following beneficial effects: the present invention atomizes the liquid in a pure ultrasonic atomization mode, thereby being free of heat conduction loss, and has low power consumption and high efficiency, the atomizer does not become hot and is energy-saving, the atomization taste is more pure, no burnt flavor is produced, and no harmful substance is produced by the heating of tobacco tar guide cotton or fibers and other tobacco tar guide materials; the structure is simple and exquisite, and the manufacture and use are convenient; and no micropore needs to be provided in the atomization piece of the present invention to eject the atomizing smoke, thereby being free of the situation that the atomizing smoke cannot be ejected because the micropore is blocked by large liquid molecules in a atomization process of the gas, and meanwhile the liquid leakage of the atomizer can be better prevented.

DETAILED DESCRIPTION OF THE INVENTION

As shown in FIG. 1, FIG. 2, FIG. 3, FIG. 7 and FIG. 8, an ultrasonic atomizer in embodiments 1, 2 and 3 of the present invention comprises an atomization piece 1; the atomization piece 1 comprises a piezoelectric ceramic layer 3; upper and lower surfaces of the piezoelectric ceramic layer 3 are respectively in contact with a first conducting layer 1A (a sliver layer) and a second conducting layer 19 (a sliver layer); the atomization piece 1 is in contact with a liquid guide structure, which guides the liquid onto the upper surface of the first conducting layer 1A; the liquid guide structure communicates with a liquid storage cavity 2; the upper surface of the first conducting layer 1A communicates with an airflow passage; or, electric conductors can also be printed on two end faces of the piezoelectric ceramic layer to form the above-mentioned atomization piece.

In embodiments 1, 2 and 3 of the present invention, the atomization piece and the liquid storage cavity are sequentially arranged along an outflow direction of an atomized gas, so that the liquid in the liquid storage cavity can conveniently flow into a tobacco tar guide structure under its own gravity force.

In embodiments 1, 2 and 3 of the present invention, the airflow passage comprises an air inlet pipe 31 and an air outlet pipe 32 provided in the air inlet pipe 31, and an air inlet passage 33 is provided between the inner wall of the air inlet pipe 31 and the outer wall of the air outlet pipe 32; the air inlet pipe 31 communicates with the air outlet pipe 32 through the air inlet passage 33; the bottom end (i.e., one end close to the atomization piece 1) of the air outlet pipe 32 communicates with the upper surface of the atomization piece 1; top ends (i.e., ends that are away from the atomization piece 1) of the air inlet pipe 31 and the air outlet pipe 32 are in fixed connection with a suction nozzle base 5 and communicate with a suction nozzle 4 on the suction nozzle base 5; an air inlet 6 is provided in the suction nozzle base 5; and the air inlet passage 33 communicates with the air inlet 6.

Figure 1:
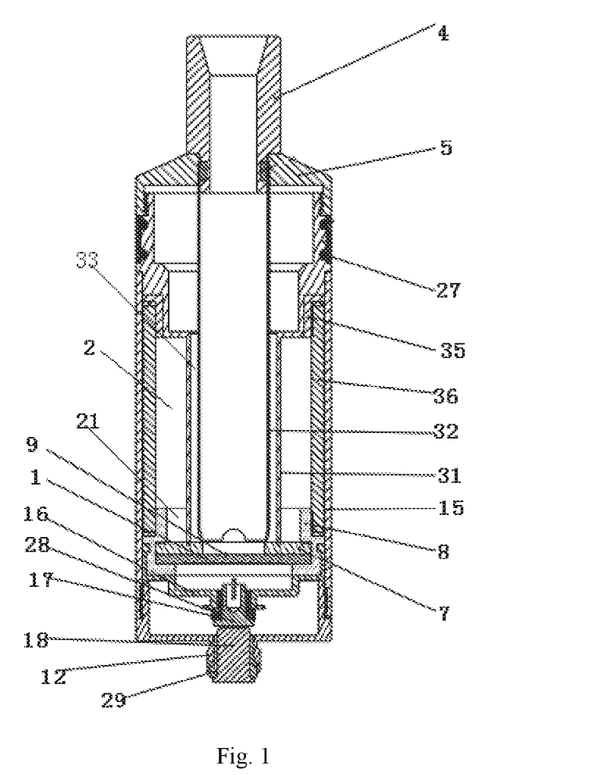
FIG. 1 is a structural schematic diagram of embodiment 1 of the present invention.
Figure 2:
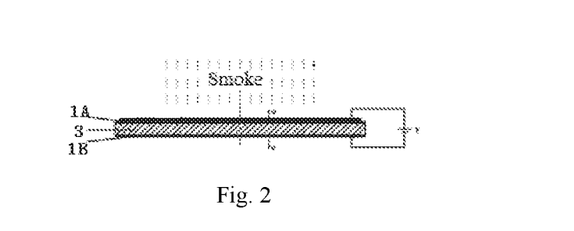
FIG. 2 is a structural schematic diagram of an atomization piece of the present invention.
Figure 7:
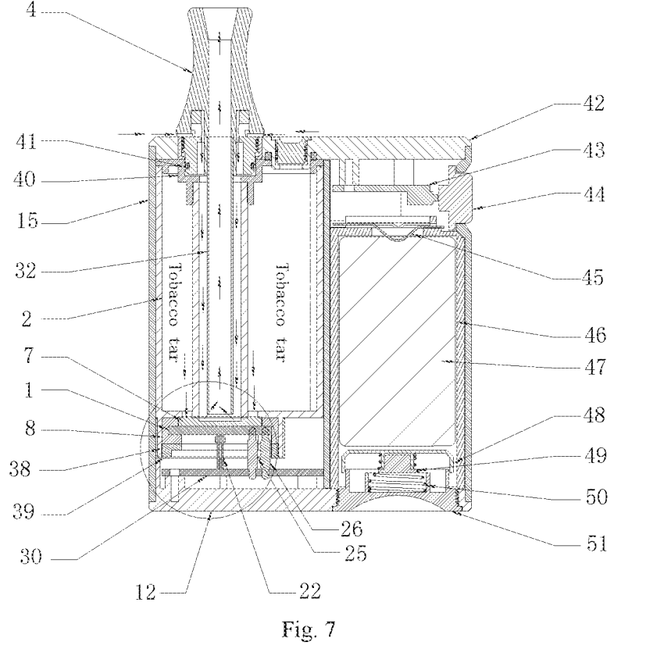
FIG. 7 is a structural schematic diagram of embodiment 2 of the present invention.
Figure 8:
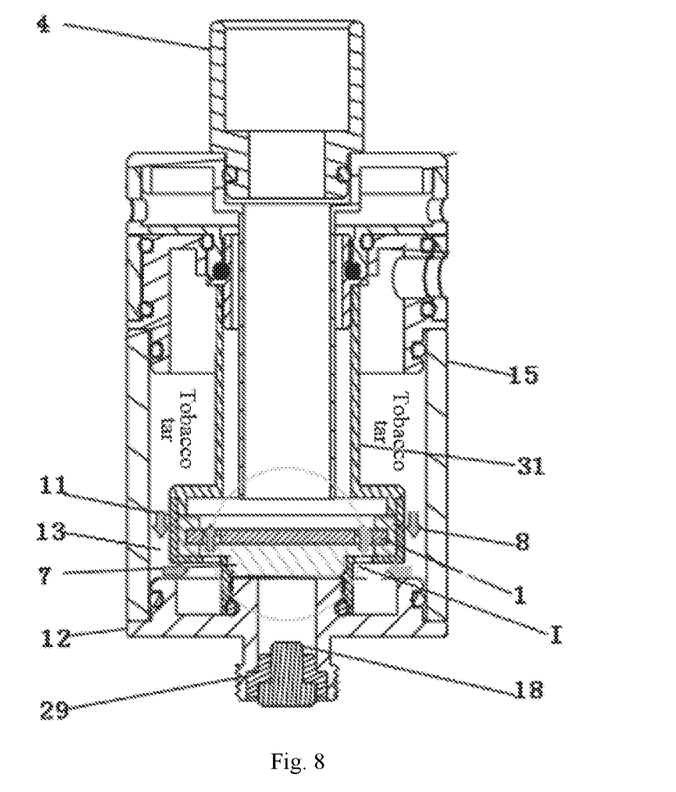
FIG. 8 is a structural schematic diagram of embodiment 3 of the present invention.

In embodiments 1, 2 and 3 of the present invention, a regulating device 27 (i.e., an air regulating ring, wherein an air regulating hole is provided in the air regulating ring in a position corresponding to the air inlet, when in use, the air regulating ring can be rotated to change the size of the air regulating hole so as to change the amount of airflow, and when the air regulating hole coincides with the air inlet, the air inflow is the maximum) which regulates the amount of the airflow of the air inlet 6 is provided on the suction nozzle base 5.

Figure 3:
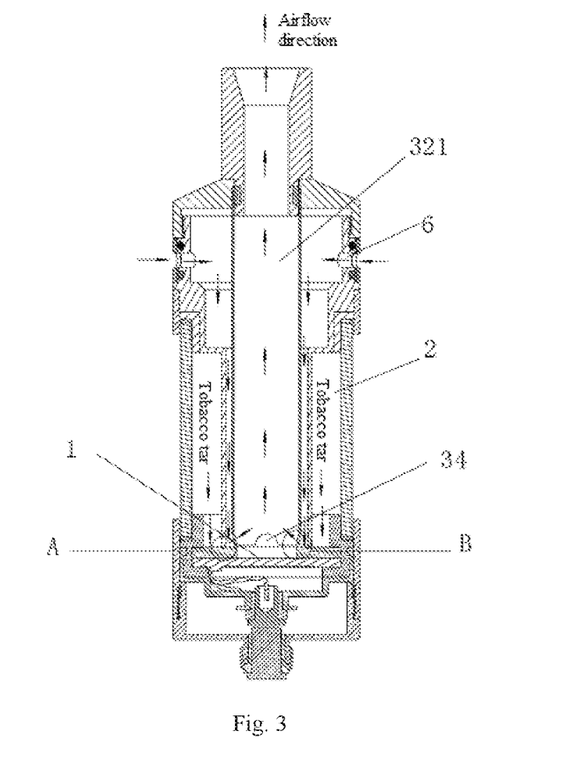
FIG. 3 is a schematic diagram of an airflow direction in embodiment 1 of the present invention.
Figure 4:
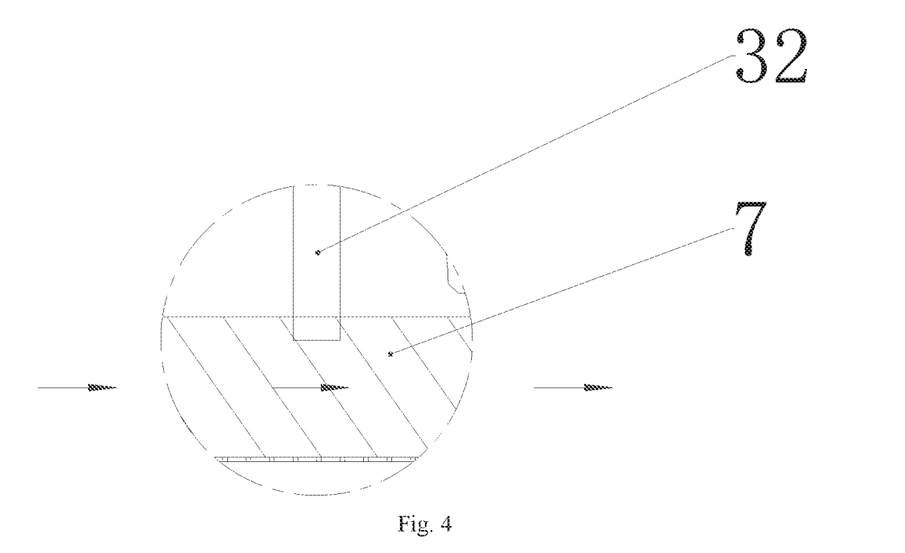
FIG. 4 is an enlarged view of part A in FIG. 3.
Figure 5:
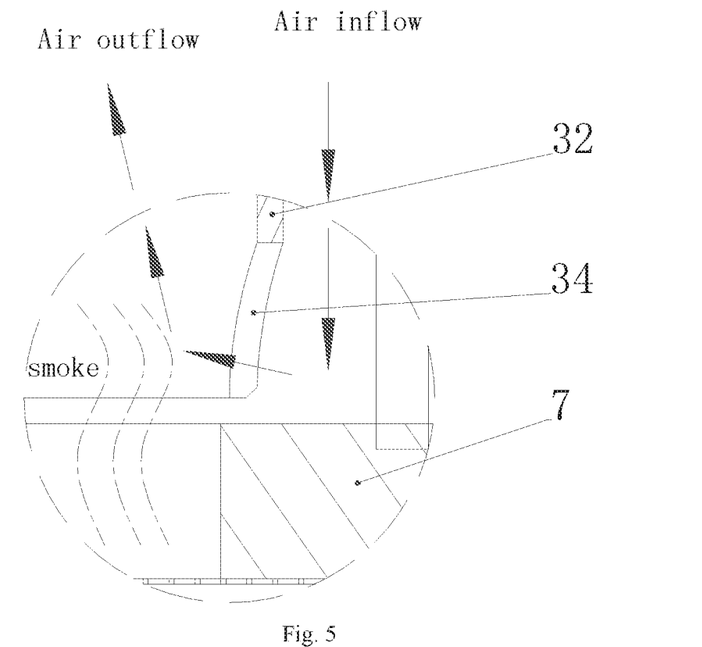
FIG. 5 is an enlarged view of part B in FIG. 3.

As shown in FIG. 3, FIG. 4 and FIG. 5, in embodiments 1 and 2 of the present invention, the liquid guide structure is in contact with the upper surface (i.e., one surface that is away from the piezoelectric ceramic layer) of the first conducting layer 1A; and the bottom end of the air outlet pipe 32 props against the upper surface of the liquid guide structure (i.e., one surface of the liquid guide structure that is away from the atomization piece), and an air inlet notch 34 is provided in the bottom end of the air outlet pipe 32. An air outlet passage 321 is provided in the air outlet pipe 32; and the air inlet passage 33 communicates with the air outlet passage 321 through the air inlet notch 34.

As shown in FIG. 5, in the present invention, interval (the interval can be regulated according to actual needs) between the bottom end of the air outlet pipe 32 and the upper surface of the atomization piece 1 is about 0.5-1.0 mm, therefore the air in the air inlet passage 33 is prevented from being blocked to fail to enter the air outlet passage 321, and the smoke can also be prevented from entering the air inlet passage 33 to affect the taste of the smoke.

In embodiments 1 and 2 of the present invention, the liquid guide structure comprises a porous material 7; the upper surface of the porous material 7 covers or fills a liquid outlet 21 in the bottom end of the liquid storage cavity 2; the porous material 7 and/or the atomization piece 1 is provided in an elastic sealing sleeve 8 (a silica gel sleeve can be used as elastic sealing sleeve), and the outer wall of the upper part (i.e., one end of the elastic sealing sleeve that is close to the liquid storage cavity) of the elastic sealing sleeve 8 is in hermetical connection with the inner wall at the bottom end (one end that is away from the suction nozzle) of the liquid storage cavity 1; and both of the liquid storage cavity 2 and the elastic sealing sleeve 8 are provided in a housing 15.

In embodiment 1, the outer wall of the upper part (one end that is close to the liquid storage cavity) of the silica gel sleeve is in hermetical connection with the inner wall of the bottom end of the liquid storage cavity, the outer wall of the lower part (one end that is away from the liquid storage cavity) of the silica gel sleeve is in contact with the inner wall of an atomization base 16, the outer wall of the atomization base 16 is in contact with the inner wall of the housing 15, and an atomization electrode 17 insulated and isolated (insulated and isolated by an atomization insulation ring 28) from the atomization base 16 is provided in the atomization base 16; the atomization base 16 is in fixed connection with the top end (one end that is close to the atomization piece) of a base 12; the outer wall of the base 12 is in screw connection with the inner wall of the housing 15; and an electrode ring 18 insulated and isolated (insulated and isolated by a base insulation ring 29) from the base 12 and is in contact with the atomization electrode 17 is fixed in the base 12.

As shown in FIG. 1, in embodiment 1, the liquid storage cavity 2 adopts a glass outer wall 36, and the inner side on the top of the glass outer wall is in contact with the outer wall of the top end of the air inlet pipe 31 through a silica gel ring 35, so that the sealing property is good.

Figure 6:
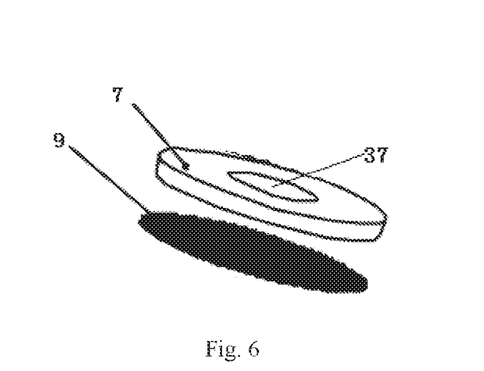
FIG. 6 is an explosive view of a tobacco tar guide structure in embodiment 1 of the present invention.

As shown in FIG. 6, in embodiment 1, a hole 37 is provided in the middle of the porous material 7, and the hole 37 is provided right below the air outlet pipe 32, so the atomized gas can be conveniently sucked out from the air outlet pipe; the lower surface, one surface that is attached to the atomization piece) of the porous material 7 (e.g., cotton or other materials which can absorb tobacco tar) is in contact with the first conducting layer 1A through a liquid guide layer 9, the liquid guide layer 9 can be a stainless steel mesh (preventing deterioration of the liquid resulting of rust) or a tobacco tar guide cotton layer.

As shown in FIG. 7, in embodiment 2, the first conducting layer 1A and the second conducting layer 1B are respectively in elastic connection example, the elastic connection can be realized by an elastic ejector pin) with a positive electrode 25 and a negative electrode 26 fixed in the base 12; and a main control board 30 is fixed in the base 12, the main control board 30 can detect the temperature of the atomization piece by a temperature sensor 22 and control the start and stop of the atomization piece (the normal working temperature of the atomization piece is 130-220° C. in general, the atomization piece should be stopped once the temperature exceeds 220° C. to prevent the atomization piece from being damaged). In the embodiment, the bottom of the silica gel sleeve is in contact with a compressing block 38, the pressing block 38 can compress silica gel sleeve tightly, and thus the atomization piece is more stable. Both of the compressing block 38 and the silica gel sleeve are fixed in a compressing sleeve 39; and the compressing sleeve 39 is provided above the main control board 30.

In embodiment 2, a tobacco tar injection hole 20 of the liquid storage cavity is provided in the top (one end close to the suction nozzle) of the liquid storage cavity (the outer wall of the liquid storage cavity can be made of a transparent glass material), the tobacco tar injection hole 20 is sealed by a hole cover 40, and the hole cover 40 is sealed with the bottom (one end that is away from the suction nozzle) of the suction nozzle base 5 through a sealing ring 41.

In embodiment 2, there is a recessed region in the middle of the upper surface of the porous material 7 (i.e., the thickness of the middle is smaller than that of the periphery), and the recessed region is located right below the air outlet pipe 32.

Figure 9:
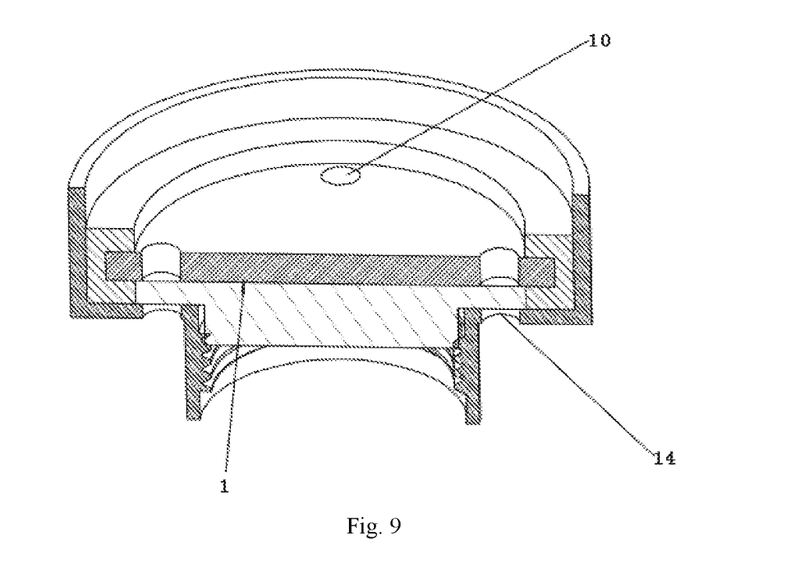
FIG. 9 is an enlarged view of part I in FIG. 8.

As shown in FIG. 8 and FIG. 9, in the embodiment 3 of the present invention, the liquid guide structure comprises the porous material 7; the upper surface of the porous material 7 is in contact with the lower surface (one surface that is away from the piezoelectric ceramic layer) of the second conducting layer 1B; a plurality of liquid guide holes 10 are provided in the atomization piece 7; both of the atomization piece 1 and the porous material 7 are provided in a mounting base 11, and the outer wall of the atomization piece 1 is in contact with the inner wall of the mounting base 11 through an elastic sealing base 8; the top end of the mounting base 11 is in fixed connection with the bottom end of the air inlet pipe 31; the bottom end of the mounting base 11 is in fixed connection with the middle (a salient at the middle of the base 12) of the base 12; the lower surface of the porous material 7 is in contact with the upper surface of the middle of the base 12 (i.e., a space between the base 12 and the atomization space is filled); the outer wall of the base 12 is in fixed connection with the inner wall of the bottom end (one end that is away from the suction nozzle) of the liquid storage cavity 2; passages 13 are provided among the mounting base 11, the inner wall of the liquid storage cavity 2 and the inner wall of the base 12; a liquid inlet 14 is provided in the bottom (one end that is away from the suction nozzle) of the mounting base 11; the liquid inlet 14 communicates with the liquid storage cavity 2 through the passages 13; and the top end of the mounting base 11 is sleeved on the bottom (one end that is away from the suction nozzle) of the air inlet pipe 31.

Correspondingly, the electronic cigarette in the present invention comprises a power supply component and the above-mentioned ultrasonic atomizer; the power supply component provides working power supply for the atomization piece 1, the temperature sensor 22 and other electronic components.

The power supply component and the ultrasonic atomizer can be vertically provided, that is, the top end of the power supply component is connected with the bottom end (one end that is opposite to the suction nozzle) of the ultrasonic atomizer.

Figure 10:
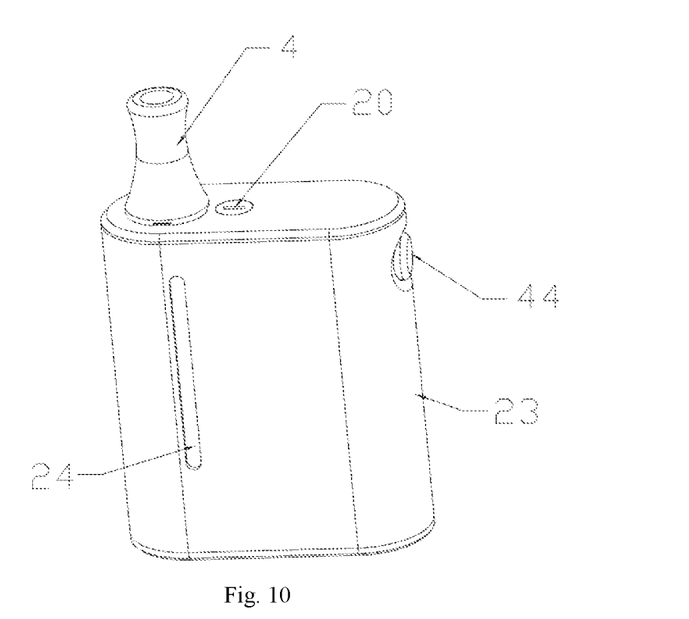
FIG. 10 is a schematic diagram of an external structure of electronic cigarette in which an atomizer and a power supply component are provided side by side.

Or, the ultrasonic atomizer and the power supply component can also be provided in a shell 23 side by side (as shown in FIG. 8 and FIG. 10). The power supply component comprises a battery bin 46, and a battery 47 is fixed in the battery bin 46; an elastic contact piece 45 is in contact with the top end of the battery 47 and applies a downward force to the battery 47, so that the battery 47 is more stable; an upper cover 42 is covered at the top of the battery bin 46, a key 44 is fixed to the battery bin 46 below the upper cover 42, and the key 44 is in contact with a key board fixed in the battery bin 46; the bottom end of the battery bin 46 is sealed by a lower cover 51, the inner wall of the lower cover 51 is in contact with one end of a compression spring 50, the other end of the compression spring is in contact with a contact cover 48, and the contact cover 48 is in contact with the bottom end of the battery 47 to further guarantee the stability of the battery; the compression spring 50 is fixed by a spring fixing ring 49; and the upper cover 42 is in fixed connection with the suction nozzle base, and the lower cover 51 is in fixed connection with the base 12. The electronic cigarette having such structure is smaller in volume and is more convenient to take.

As shown in FIG. 10, to facilitate observing the volume of the liquid in the liquid storage cavity (the liquid storage cavity adopts a transparent outer wall) to judge whether the liquid needs to be supplemented, a liquid storage cavity observation window 24 is provided in the shell 23.

The working principle of the present invention is as follows: when a smoker smokes, the air enters the air inlet passage from the air inlet and enters the air outlet pipe from the bottom of the air inlet passage, meanwhile, the atomization piece vibrates to atomize the tobacco tar on its surface, and after passing through the air outlet pipe, the atomized gas together with the external air is inhaled by the smoker.

The invention claimed is:

1. An ultrasonic atomizer, wherein the ultrasonic atomizer comprises an atomization piece and a liquid guide structure, which guides liquid onto the upper surface of the atomization piece; the liquid guide structure communicates with a liquid storage cavity; an upper surface of the atomization piece communicates with an airflow passage; and the atomization piece comprises a piezoelectric ceramic layer and an electric conductor, which drives vibration of the piezoelectric ceramic layer.

2. The ultrasonic atomizer of claim 1, wherein the atomization piece and the liquid storage cavity are sequentially arranged along an outflow direction of an atomized gas.

3. The ultrasonic atomizer of claim 2, wherein the airflow passage comprises an air inlet pipe and an air outlet pipe provided in the air inlet pipe, and an air inlet passage is provided between an inner wall of the air inlet pipe and an outer wall of the air outlet pipe; the bottom end of the air outlet pipe communicates with the upper surface of the atomization piece; top ends of the air inlet pipe and the air outlet pipe are in fixed connection with a suction nozzle base, and the air outlet pipe communicates with a suction nozzle on the suction nozzle base; an air inlet is provided in the suction nozzle base; and the air inlet passage communicates with the air inlet.

4. The ultrasonic atomizer of claim 3, wherein the liquid guide structure is in contact with the upper surface of the atomization piece; the bottom end of the air inlet pipe props against the upper surface of the liquid guide structure, and an air inlet notch is provided in the bottom end of the air outlet pipe; an air outlet passage is provided in the air outlet pipe; and the air inlet passage communicates with the air outlet passage through the air inlet notch.

5. The ultrasonic atomizer of claim 4, wherein the liquid guide structure comprises a porous material; an upper surface of the porous material covers or fills a liquid outlet in a bottom end of the liquid storage cavity; the atomization piece is provided in an elastic sealing sleeve, and an outer wall of the upper part of the elastic sealing sleeve is in hermetical connection with an inner wall of the bottom end of the liquid storage cavity; and both of the liquid storage cavity and the elastic sealing sleeve are provided in a housing.

6. The ultrasonic atomizer of claim 5, wherein a hole is provided in the middle of the porous material, and the hole is provided below the air outlet pipe; and a lower surface of the porous material is in contact with the lower surface of the atomization piece through a liquid guide layer.

7. The ultrasonic atomizer of claim 5, wherein there is a recessed region in the middle of an upper surface of the porous material, and the recessed region is located below the air outlet pipe.

8. The ultrasonic atomizer of claim 3, wherein the liquid guide structure comprises the porous material; the upper surface of the porous material is in contact with the lower surface of the atomization piece; and a plurality of liquid guide holes are provided in the atomization piece.

9. The ultrasonic atomizer of claim 8, wherein the atomization piece is provided in a mounting base; a top end of the mounting base is in fixed connection with a bottom end of the air inlet pipe; the bottom end of the mounting base is in fixed connection with the middle of a base; the lower surface of the porous material is in contact with the upper surface of the middle of the base; the outer wall of the base is in fixed connection with the inner wall of the bottom end of the liquid storage cavity; passages are provided among the mounting base, the inner wall of the liquid storage cavity and the inner wall of the base; a liquid inlet is provided in the bottom of the mounting base; and the liquid inlet communicates with the liquid storage cavity through the passages.

10. The ultrasonic atomizer of claim 8, wherein the electric conductor is in elastic connection with a positive electrode and a negative electrode fixed in the base.

11. The ultrasonic atomizer of claim 3, wherein a regulating device which regulates an amount of the airflow of the air inlet is provided on the suction nozzle base.

12. The ultrasonic atomizer of claim 11, wherein a tobacco tar injection hole is provided in the liquid storage cavity.

13. The ultrasonic atomizer of claim 12, wherein the atomization piece is in contact with a temperature sensor.

14. An electronic cigarette, comprising a power supply component, wherein the electronic cigarette further comprises the ultrasonic atomizer of claim 13; and the power supply component provides working power supply for the atomization piece and the temperature sensor.

15. The electronic cigarette of claim 14, wherein a top end of the power supply component is connected with the bottom end of the ultrasonic atomizer.

16. The electronic cigarette of claim 14, wherein the ultrasonic atomizer and the power supply component are provided in a shell side by side.

17. The electronic cigarette of claim 16, wherein a liquid storage cavity observation window is provided in the shell on the outer side of the liquid storage cavity.

* * * * *